(12) United States Patent
Shutske et al.

(10) Patent No.: US 6,248,750 B1
(45) Date of Patent: Jun. 19, 2001

(54) 9-HYDROXYAMINO TETRAHYDROACRIDINE AND RELATED COMPOUNDS

(75) Inventors: Gregory Michael Shutske, Flemington; Kevin James Kapples, Little York, both of NJ (US)

(73) Assignee: Hoechst Roussel Pharmaceuticals, Bridgewater, NJ (US)

( * ) Notice: Subject to any disclaimer, the term of this patent is extended or adjusted under 35 U.S.C. 154(b) by 0 days.

(21) Appl. No.: 09/534,716

(22) Filed: Mar. 24, 2000

Related U.S. Application Data

(62) Division of application No. 08/259,739, filed on Jun. 13, 1994, now Pat. No. 6,075,144, which is a continuation of application No. 08/041,346, filed on Apr. 1, 1993, now abandoned, which is a continuation of application No. 07/670,631, filed on Mar. 18, 1991, now abandoned, which is a continuation-in-part of application No. 07/039,883, filed on Apr. 20, 1987, now abandoned.

(51) Int. Cl.$^7$ .................. A61K 31/44; C07D 219/10; C07D 221/06; C07D 221/16; C07D 221/22

(52) U.S. Cl. ................ 514/290; 514/297; 546/105; 546/106; 546/93; 546/79

(58) Field of Search .................... 546/105, 106, 546/93, 79; 514/290, 297

(56) References Cited

U.S. PATENT DOCUMENTS

| | | | |
|---|---|---|---|
| 3,232,945 | 2/1966 | Segal, Jr. et al. ............ | 260/287 |
| 3,318,895 | 5/1967 | Pribyl et al. ............ | 514/297 |
| 3,318,896 | 5/1967 | Pribyl et al. ............ | 514/290 |
| 3,541,066 | 11/1970 | Wolf ............ | 260/294.7 |
| 3,580,915 | 5/1971 | Wolf et al. ............ | 260/286 |
| 3,637,706 | 1/1972 | Wolf et al. ............ | 260/268 |
| 3,647,800 | 3/1972 | Wolf et al. ............ | 260/287 |
| 3,657,233 | 4/1972 | Wolf et al. ............ | 424/248 |
| 3,674,790 | 7/1972 | Wolf et al. ............ | 260/288 |
| 3,987,047 | 10/1976 | Griss et al. ............ | 260/287 |
| 4,108,998 | 8/1978 | Demerson et al. ............ | 424/258 |
| 4,631,286 | 12/1986 | Shutske et al. ............ | 514/297 |
| 4,695,573 | 9/1987 | Shutske et al. ............ | 514/290 |
| 4,816,456 | 3/1989 | Summers et al. ............ | 514/255 |
| 4,851,536 | 7/1989 | Skotnicki et al. ............ | 546/106 |
| 4,868,177 | 9/1989 | Shutske et al. ............ | 514/228.2 |
| 4,985,430 | 1/1991 | Morita et al. ............ | 514/253 |
| 5,336,485 | 8/1994 | Fariss et al. ............ | 424/10 |

FOREIGN PATENT DOCUMENTS

| | | |
|---|---|---|
| 0 179 383 | 4/1986 | (EP) . |
| 0 268 871 | 6/1988 | (EP) . |
| 0 288 852 | 11/1988 | (EP) . |
| 1022940 | 3/1966 | (GB) . |
| WO 89/0239 | 4/1989 | (WO) . |
| 9222534 | * 12/1992 | (WO) . |

OTHER PUBLICATIONS

Okano T. et al. "Syn. of 9–Cl–&9–nitro–hydroacrid. 10–oxides", Yakugaku Zasshi, 89/9, 1309–7, Sep. 1969.*
Hendrickson et al. "Ident.of 9–OH–hydroacrid.as a hepatic . . . " J. Chrom. 487/2, 401–8, Sep. 1969.*
E.S. Abramochkin and M.E. Koshin; Khimiko–Farmatsevticheskii Zhurnal,4, 10 (1970), published in the Soviet Union, translated into English in Pharmaceutical Chemistry Journal,4, 372 (1970) and entitled "Synthesis of N–Substituted 4–Amino–2,3–pentamethylenequinolines".
M.A. Konshin and P.A. Petyunin, Khimiko–Farmatsevticheskii Zhurnal,5, 10 (1971), published in the Soviet Union, translated into English in Pharmaceutical Chemistry Journal,5, 654 (1971) and entitled "Synthesis and Biological Action of 9–Alkylamino–1,2,3,4–tetrahydroacridines".
M.E. Konshin, et al., Izv. Vyssh, Ucheb. Zaved. Khim. Khim. Tekhnol., 15, 243 (1972) published in Soviet Union, and English translation thereof and entitled "Synthesis of 4–(α–pyridylamino)–2,3–Polymethylenequinolines".
M.E. Konshin, et al., Izv. Vyssh, Ucheb. Zaved. Khimiya i Khimicheskaya Tekhnologiya, 15, 726 (1972) published in Soviet Union, and English translation thereof and entitled "Synthesis of 7–methyl–9–Alkylamino–1,2,3,4–tetrahydroacridines".
M.E. Konshin, et al., Khimiya Geterotsiklicheskikh Soyedineniy, 4, 531 (1973) and published in Soviet Union, and English translation thereof and entitled "Investigation of 2,3–polymethylenequinolines XIV. 9–Alkylamino–β–quinindans".

(List continued on next page.)

Primary Examiner—Richard L. Raymond
Assistant Examiner—Sudhaker B. Patel
(74) Attorney, Agent, or Firm—Frommer Lawrence & Haug LLP

(57) ABSTRACT

There are disclosed compounds having the formula

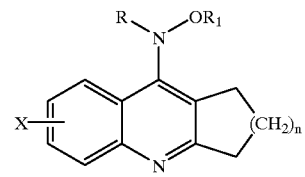

wherein n is 1–4; X is hydrogen, loweralkyl, cycloalkyl, loweralkoxy, halogen, hydroxy, nitro, trifluoromethyl, formyl, loweralkylcarbonyl, arylcarbonyl, —SH, loweralkylthio, —NHCOR$_2$ or —NR$_3$R$_4$ where R$_2$ is hydrogen or loweralkyl, and R$_3$ and R$_4$ are independently hydrogen, loweralkyl or cycloalkyl; R is hydrogen, loweralkyl or loweralkylcarbonyl; and R$_1$ is hydrogen, loweralkyl, aryl, diloweralkylaminoloweralkyl, arylloweralkyl, furylloweralkyl, thienylloweralkyl, pyridinylloweralkyl, diarylloweralkyl, oxygen-bridged arylloweralkyl or oxygen-bridged diarylloweralkyl; stereo, optical and geometrical isomers thereof, and pharmaceutically acceptable acid addition salts thereof which are useful for enhancing memory.

14 Claims, No Drawings

OTHER PUBLICATIONS

M.E. Konshin, et al., Khimiko–Farmatsevticheskii Zhurnal, 8, 17 (1974) and published in Soviet Union, and translated into English and entitled "2,3–Polymethylenequinolines and Biological Activity of 4–Amino–2,3–Polymethylenequinolines".

M.E. Konshin, Nauch. Tr. Perm. Farmstsevt. In–t, 10, 6 (1976) published in the Soviet Union; (getting translation).

V.A. Khaldeeva and M.E. Koshin, Khimiya Geterotsiklicheskikh Soedinenii, 2, 263 (1976) published in Soviet Union, and English translation thereof and entitled "Naphthyridines VII. Synthesis of 10–Alkylamino–1,2,3,4–Tetrahydrobenzo[b]–1,6–Naphthyridines".

J. Bielavsky, Collection Czechoslov. Chem. Communication, 42, 2802 (1977) published in the Czech Republic and entitled "Analogues of 9–Amino–1,2,3,4–tetrahydroacridine".

K.C. Joshi and K. Dubey, Indian Journal of Chemistry, 16B, 156 (1978), published in India, and entitled "Possible Psychopharmacological Agents: Part I—Synthesis of Some Fluorine Containing 9/10–Substituted Cyclopenta[b]quinolines & Cyclohexa[b]quinolines".

G.K. Patnaik, et al., Journal of Medicinal Chemistry, vol. 7 483 (1966) published in the United States and entitled "Compounds acting on the Central Nervous System. IV. 4–Substituted 2,3–Polymethylenequinolines".

H.P. Hendrickson, et al. Chemical Abstract, 110, 185270u (1989) published in the United States and (getting copy).

G.M. Shutske, Chemical Abstracts, 110, 95025p (1988) and entitled "9–(Hydroxyamino)tetrahydroacridines, a process for their preparation, and their use as medicaments for treatment of Alzheimer disease".

R.E. McMahon, in Alfred Burger Medicinal Chemistry, $3^{rd}$ Edition, Part I, Wiley–Interscience, New York, 1970, pp. 50 to 63, published in the United States and entitled "Drug Metabolism".

H.P. Hendrickson, et al., Journal of Chromatography, 487, 401 (1989) published in the Netherlands and entitled "Identification of 9–Hydroxylamino–1,2,3,4–tetrahydroacridine as a Hepatic Microsomal Metabolite of Tacrine by High–Performance Liquid chromatography and Electrochemistry".

Tanouye, Wall Street Journal, 11 B5 91992) published in the United States and entitled "Alzheimer's Drug Still Faces Skepticism Despite Study Showing Modest Benefits".

W.K. Summers, et al., Biological Psychiatry, 16, 145 (1981) and entitled "Use of THA in Treatment of Alzheimer–Like Dementia; Pilot Study in Twelve Patients".

W.K. Summers, et al., Clinical Toxicology, 16, 269 (1980) published in the United States and entitled "THA—A Review of the Literature of Five Overdose Patients".

Remington Pharmaceutical Sciences, J.E. Hoover, Managing Editor, $15^{th}$ Edition, Mark Publishing Company, Easton, PA, 1975, p. 466.

* cited by examiner

9-HYDROXYAMINO TETRAHYDROACRIDINE AND RELATED COMPOUNDS

This is a divisional of U.S. patent application Ser. No. 08/259,739 filed Jun. 13, 1994, now U.S. Pat. No. 6,075,144 granted Jun. 13, 2000, which is a continuation of U.S. patent application Ser. No. 08/041,346 filed Apr. 1, 1993, now abandoned, which is a continuation of U.S. patent application Ser. No. 07/670,631 filed Mar. 18, 1991, now abandoned, which is a continuation-in-part of a prior application, Ser. No. 07/039,883, filed Apr. 20, 1987, now abandoned.

This ivention relates to compounds having the formula,

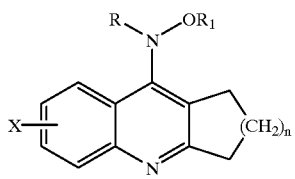

(I)

wherein n is 1–4; X is hydrogen, loweralkyl, cycloalkyl, loweralkoxy, halogen, hydroxy, nitro, trifluoromethyl, formyl, loweralkylcarbonyl, arylcarbonyl, —SH, loweralkylthio, NHCOR$_2$ or —NR$_3$R$_4$ where R$_2$ is hydrogen or loweralkyl, and R$_3$ and R$_4$ are independently hydrogen, loweralkyl or cycloalkyl; R is hydrogen, loweralkyl or loweralkylcarbonyl; and R$_1$ is hydrogen, loweralkyl, aryl, diloweralkylaminoloweralkyl, arylloweralkyl, furylloweralkyl, thienylloweralkyl, pyridinylloweralkyl, diarylloweralkyl, oxygen-bridged arylloweralkyl or oxygen-bridged diarylloweralkyl; stereo, optical and geometrical isomers thereof, and pharmaceutically acceptable acid addition salts thereof which are useful for enhancing memory, methods for synthesizing them, and pharmaceutical compositions comprising an effective memory enhancing amount of such a compound, and a method of increasing the cholinergic function in mammals which comprises the adminstration of an effective amount of such a compound.

Throughout the specification and the appended claims, a given chemical formula or name shall encompass all stereo, optical and tautomeric isomers thereof where such isomers exist, as well as pharmaceutically acceptable acid addition salts thereof and solvates thereof such as for instance hydrates. Thus, for instance, where the group R of Compound I is hydrogen, Formula Ia should be considered as equivalent to its tautomeric form Ib. Thus, in terms of nomenclature, N-methoxy-1,2,3,4-tetrahydro-9-acridinamine, for instance, should be considered as equivalent to N-methoxy-1,2,3,4-tetrahydroacrdin-9(10H)-imine.

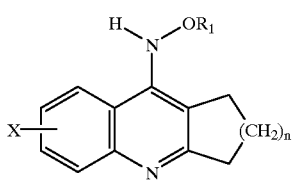

(Ia)

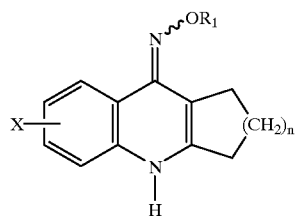

(Ib)

The following definitions shall apply throughout the specification and the appended claims.

Unless otherwise stated or indicated, the term loweralkyl denotes a straight or branched alkyl group having from 1 to 6 carbon atoms. Examples of said alkyl include methyl, ethyl, n-propyl, iso-butyl, pentyl, and hexyl.

Unless otherwise stated or indicated, the term cycloalkyl denotes a saturated ring containing 3 to 7 carbon atoms. Examples of said cycloalkyl include cyclopropyl, cyclohexyl and cycloheptyl.

Unless otherwise stated or indicated, the term loweralkoxy denotes a straight or branched alkoxy group having 1 to 6 carbon atoms. Examples of said alkoxy include methoxy, ethoxy, iso-propoxy, sec-butoxy, and straight and branched chain hexyloxy.

Unless otherwise stated or indicated, the term halogen shall mean fluorine, chlorine, bromine or iodine.

Unless otherwise stated or indicated, the term aryl shall mean an unsubstituted phenyl group, a phenyl group substituted with 1, 2 or 3 substituents each of which being independently loweralkyl, loweralkoxy, halogen, hydroxy, trifluoromethyl, phenyl or benzyloxy.

Unless otherwise stated or indicated, the term oxygen-bridged shall signify the fact that an oxygen atom is present between aryl and ldweralkyl groups and/or an oxygen atom has replaced a methylene group in the loweralkyl group, with the proviso that said methylene group is not alpha to the amino nitrogen carrying the groups R and R$_1$. Thus, for instance, examples of oxygen-bridged arylloweralkyl include 3-phenoxypropyl and 4-phenoxybutyl, and examples of oxygen-bridged diarylloweralkyl include 2-[bis(4-fluorophenyl)methoxy] ethyl and 2-[bis(3-fluorophenyl) methoxy] ethyl.

The compounds of this invention are prepared as described below. The required O-substituted hydroxylamines of formula II wherein R is hydrogen and R$_1$ is not hydrogen are, in some cases, commercially available and, where not, can readily be prepared by one skilled in the art by means of the alkylation and subsequent hydrolysis of N-hydroxyphthalimide as disclosed by A. Rougny and M. Daudon, Bull. Soc. Chim. France, 833 (1976). Further alkylation by methods known to one skilled in the art allows the preparation of the compounds of formula II wherein R is loweralkyl and R$_1$ is not hydrogen.

In order to simplify the description of the synthetic schemes, the description will be presented with specific reference to the situation where n=2, but it will readily be understood that the synthetic schemes can also be applied to the other situations by making obvious modifications where necessary.

Throughout the description of the synthetic steps, definitions of X, R and R$_1$ through R$_4$ are as given above unless otherwise stated or indicated.

A compound of formula IV wherein R is not loweralkylcarbonyl can be prepared by reacting a compound of formula III with a hydroxylamine of formula II. Said reaction can be conducted at a temperature of 120–220° C. in the presence of a hydroxylated aromatic compound such as phenol or cresol.

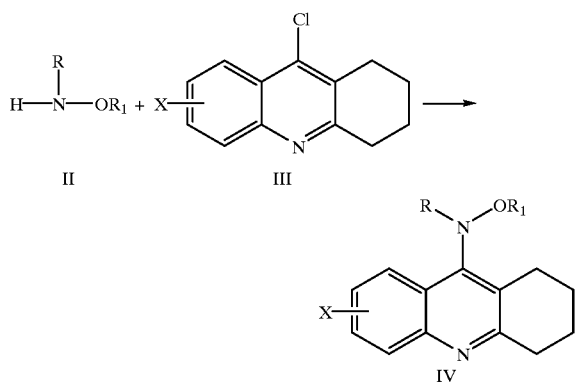

A compound of formula IVb wherein R is loweralkylcarbonyl can be prepared by reacting a compound of formula IVa with an acylating agent such as an acid halide or anhydride of formula V wherein $R_5$ is loweralkyl and Y is chlorine, bromine or $OC(=O)R_5$. The reaction can be carried out in an inert solvent such as chloroform, methylene chloride, toluene, tetrahydrofuran or diethyl ether in the presence of a proton acceptor such as pyridine, 4-dimethylamninopyridine, triethylamine or diisopropylethylamine at a temperature of 0–100° C.

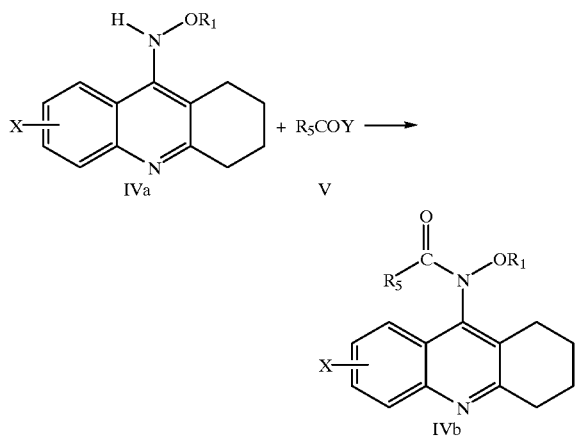

The compounds of Formula I of the present invention can be used for the treatment of various memory dysfunctions characterized by decreased cholinergic function, such as Alzheimer's disease.

This utility can be ascertained by determining the ability of these compounds to inhibit the activity of the enzyme acetylcholinesterase and thereby increase the acetylcholine levels in the brain.

CHOLINESTERASE INHIBITION ASSAY

The ability to inhibit acetylchlinesterase was determined by the photometric method of Ellman et al., Biochem. Pharmacol. 7, 88 (1961). Results of some of the compounds of this invention are presented in Table 1 below along with a result of a reference compound.

TABLE 1

Cholinesterase Inhibition

| Compound | $IC_{50}$ (molar conc.) |
|---|---|
| N-methoxy-1,2,3,4-tetrahydro-9-acridinamine | $5.1 \times 10^{-7}$ |
| N-benzyloxy-1,2,3,4-tetrahydro-9-acridinamine | $6.1 \times 10^{-6}$ |
| N-propyloxy-1,2,3,4-tetrahydro-9-acridinamine | $8.3 \times 10^{-7}$ |
| N-methyl-N-methoxy-1,2,3,4-tetrahydro-9-acridinamine | $2.7 \times 10^{-5}$ |
| N-(2-fluorobenzyloxy)-1,2,3,4-tetrahydro-9-acridinamine | $5.2 \times 10^{-6}$ |
| Reference Compound | |
| 9-Amino-1,2,3,4-tetrahydroacridine | $3.1 \times 10^{-7}$ |

This utility can also be ascertained by determining the ability of these compounds to restore cholinergically deficient memory in the Dark Avoidance Assay. In this assay mice are tested for their ability to remember an unpleasant stimulus for a period of 24 hours. A mouse is placed in a chamber that contains a dark compartment; a srong incandescent light drives it to the dark compartment, where an electric shock is administered through metal plates on the floor. The animal is removed from the testing apparatus and tested again, 24 hours later, for the ability to remember the electric shock.

If scopolamine, an anticholinergic that is known to cause memory impairment, is administered before an animal's initial exposure to the test chamber, the animal re-enters the dark compartment shortly after being placed in the test chamber 24 hours later. This effect of scopolamine is blocked by an active test compound, resulting in a greater interval before re-entry into the dark compartment.

The results for active compounds are expressed as the percent of a group of animals in which the effect of scopolamine is blocked, as manifested by an increased interval between being placed in the test chamber and re-entering the dark compartment. Results of Dark Avoidance Assay for representative compounds of this invention and a reference compound are presented in Table 2.

TABLE 2

Dark Avoidance Assay

| Compound | % Animals with Scopolamine Induced memory deficit reversed | Dose (mg/kg) (s.c.) |
|---|---|---|
| N-methoxy-1,2,3,4-tetrahydro-9-acridinamine | 27% | 1.0 |
| N-methoxy-N-methyl-1,2,3,4-tetrahydro-9-acridinamine | 27% | 1.0 |
| Reference Compound | | |
| 9-amino-1,2,3,4-tetrahydroacridine | 20% | 0.31 |

Effective quantities of the compounds of the invention may be administered to a patient by any of the various methods, for example, orally as in capsules or tablets, parenterally in the form of sterile solutions or suspensions, and in some cases intravenously in the form of sterile solutions. The free base final products, while effective themselves, may be formulated and administered in the form of their pharmaceutically acceptable acid addition salts for purposes of stability, convenience of crystallization, increased solubility and the like.

Acids useful for preparing the pharmaceutically acceptable acid addition salts of the invention include inorganic acids such as hydrochloric, hydrobromic, sulfuric, nitric, phosphoric and perchloric acids, as well as organic acids such as tartaric, citric, acetic, succinic, maleic, fumaric and oxalic acids.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compound, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0–300 milligrams of active compound.

The tablets, pills, capsules, troches and the like may also contain the following ingredients: a binder such as microcrystalline cellulose, gum tragacanth or gelatin; an excipient such as starch or lactose, a disintegrating agent such as alginic acid, Primogel, cornstarch and the like; a lubricant such as magnesium stearate or Sterotex; a glidant such as colloidal silicon dioxide; and a sweetening agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus tablets or pills may be coated with sugar, shellac, or other enteric coating agents. A syrup may contain, in addition to the active compounds, sucrose as a sweetening agent and certain preservatives, dyes, coloring and flavors. Materials used in preparing these various compositions should be pharmaceutically pure and non-toxic in the amounts used.

For the purpose of parenteral therapeutic administration, the active compounds of the invention may be incorporated into a solution or suspension. These preparations should contain at least 0.1% of active compound, but may be varied between 0.5 and about 30% of the weight thereof. The amount of active compound in such compositions is such that a suitable dosage will be obtained. Preferred compositions and preparations according to the present invention are prepared so that a parenteral dosage unit contains between 0.5 to 100 milligrams of active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparations can be enclosed in disposable syringes or multiple dose vials made of glass or plastic.

Examples of the compounds of this invention include: N-hydroxy-1,2,3,4-tetrahydro-9-acridinamine; 6-chloro-N-hydroxy-1,2,3,4-tetrahydro-9-acridinamine; N-hydroxy-7-methoxy-1,2,3,4-tetrahydro-9-acridinamine; N-methoxy-1,2,3,4-tetrahydro-9-acridinamine; N-ethoxy-7-methyl-1,2,3,4-tetrahydro-9-acridinamine; N-(benzyloxy)-1,2,3,4-tetrahydro-9-acridlnamine; N-(2-furylmethoxy-1,2,3,4-tetrahydro-9-acridinamine; N-[(2-phenylethyl)oxy]-1,2,3,4-tetrahydro-9-acridinamine; N-[(4,4-diphenylbutyl)oxy]-1,2,3,4-tetrahydro-9-acridinamine; N-[(2-dimethylaminoethyl)oxy]-1,2,3,4-tetrahydro-9-acridinamine; N-[(3-phenoxypropyl)oxy]-1,2,3,4-tetrahydro-9-acridinamine; N-methoxy-7,8,9,10-tetrahydro-6H-cyclohepta[b]quinoline-11-amine; N-benzyloxy-2,3-dihydro-1H-cyclopenta[b]quinolin-9-amine; N-methyloxy-N-methyl-1,2,3,4-tetrahydro-9-acridinamine; N-propyloxy-1,2,3,4-tetrahydro-9-acridinamine; and N-(2-fluorobenzyloxy)-1,2,3,4-tetrahydro-9-acridinamine.

The following examples are presented in order to illustrate this invention.

EXAMPLE 1

N-Methoxy-1,2,3,4-tetrahydro-9-acridinamine hydrochloride

A mixture of 9-chloro-1,2,3,4-tetrahydroacridine (4.35 g) and methoxylamine hydrochloride (2.5 g) in 100 ml of n-propanol was heated at reflux for 22 hours. The reaction mixture was then added to an iced sodium bicarbonate solution and extracted with ethyl acetate (3×). The combined organics were washed with water and dried (saturated NaCl, $MgSO_4$).

The mixture was passed through a column of florisil (10% ethyl acetate/dichloromethane) to give 3.5 g of an oil which was dissolved in methanol, treated with ethereal hydrochloric acid followed by additional ether to crystallize 2.88 g of an off-white powder, m.p. 213–214° C. dec.

| ANALYSIS: | | | |
|---|---|---|---|
| Calculated for $C_{14}H_{16}N_2O \cdot HCl$: | 63.51% C | 6.47% H | 10.58% N |
| Found: | 63.18% C | 6.37% H | 10.41% N |

EXAMPLE 2

N-Methoxy-N-methyl-1,2,3,4-tetrahydro-9-acridinamnine hydrochloride

A mixture of 9-chloro-1,2,3,4-tetmhydroacridine (5.70 g) and N,O-dimethylhydroxylamine hydrochloride (3.07 g) in 100 ml of n-propanol was heated at reflux for 24 hours. The reaction mixture was then added to an iced sodium bicarbonate solution and extracted with ethyl acetate (3×). The combined organics were washed with water and dried (saturated NaCl, $MgSO_4$).

The mixture was passed through a column of florisil (ethyl acetate) to give 4.50 g of an oil, which was purified via flash chromatography (2% ethyl acetate/dichloromethane) to give 2.4 g of an oil. This was combined with 1.0 g of crop obtained from a similar batch, and the combined material was dissolved in methanol and treated with an ethereal hydrochloric acid solution. The solution was filtered and concentrated and the residue was twice recrystallized from methanol/ethyl ether to give 1.43 g of an off-white solid, m.p. 184–187° C. dec.

ANALYSIS:

| | | | |
|---|---|---|---|
| Calculated for $C_{14}H_{16}N_2O·HCl$: | 64.62% C | 6.87% H | 10.05% N |
| Found: | 64.61% C | 6.82% H | 9.79% N |

EXAMPLE 3

N-Propyloxy-1,2,3,4-tetrahydro-9-acridinamine, oxalate, hemihydrate

A mixture of 9-chloro-1,2,3,4-tetrthydroacridine (5.26 g) and propyloxyamine hydrochloride (4.05 g) in 100 ml of n-propanol was heated at reflux for 22 hours. The reaction mixture was then added to an iced ammonium hydroxide solution and extracted with ethyl acetate (3×). The combined organics were washed with water and dried (saturated NaCl, MgSO$_4$).

The mixture was passed through a column of florisil (dichloromethane; ethyl acetate) to give 4.35 g of an oil, which was purified via flash chromatography to give 2.4 g of an oil. This was dissolved in methanol and treated with 1.1 equivalents of oxalic acid to give 1.88 g of an off-white powder, m.p. 139–142° C.

ANALYSIS:

| | | | |
|---|---|---|---|
| Calculated for $C_{14}H_{16}N_2O·C_4H_4O_4·0.5H_2O$: | 60.83% C | 6.52% H | 7.88% N |
| Found: | 60.94% C | 6.13% H | 8.00% N |

EXAMPLE 4

N-Benzyloxy-1,2,3,4-tetrahydro-9-acridinamine

A mixture of 9-chloro-1,2,3,4-tetrahydroacridine (5.03 g) and O-benzylhydroxylamine hydrochloride (4.61 g) in 100 ml of n-propanol was heated at reflux for 66 hours. The reaction mixture was then added to an iced sodium bicarbonate solution and extracted with ethyl acetate (3×). The combined organics were washed with water and dried (saturated NaCl, MgSO$_4$).

The mixture was passed through a column of florisil (10% ethyl acetate/dichloromethane) to give 7.0 g of a yellow solid. A 3.9 g portion of this was recrystallized from methanol/water to give 2.44 g of a tan solid, m.p. 106–108° C.

ANALYSIS:

| | | | |
|---|---|---|---|
| Calculated for $C_{20}H_{20}N_2O$: | 78.91% C | 6.62% H | 9.21% N |
| Found: | 79.03% C | 6.71% H | 9.19% N |

EXAMPLE 5

N-(2-Fluorobenzyloxy)-1,2,3,4-tetrahydro-9-acridinamine

A mixture of 9-chloro-1,2,3,4-tetrahydroacridine (6.18 g) and O-(2-fluorobenzyl)hydroxylamine hydrochloride (5.5 g) in 125 ml of n-propanol was heated at reflux for 20 hours. The reaction mixture was then added to an iced sodium bicarbonate solution and extracted with ethyl acetate (3×). The combined organics were washed with water and dried (saturated NaCl, MgSO$_4$).

The mixture was purified via flash chromatography (5% ethyl acetate/dichloromethane to give 6.15 g of a tan solid. This was recrystallized from methanol/water to give 4.90 g of yellow crystals, m.p. 139–141° C.

ANALYSIS:

| | | | |
|---|---|---|---|
| Calculated for $C_{20}H_{19}FN_2O$: | 74.51% C | 5.94% H | 8.69% N |
| Found: | 74.44% C | 5.91% H | 8.60% N |

I claim:

1. A pharmaceutical composition for enhancing the cholinergic function in a mammal which comprises an effective cholinergic function enhancing amount of a compound of the formula

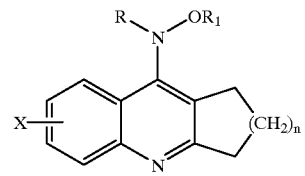

wherein n is 1–4; X is hydrogen, loweralkyl, cycloalkyl, loweralkoxy, halogen, hydroxy, nitro, trifluoromethyl, formyl, loweralkylcarbonyl, arylcarbonyl, —SH, loweralkythio, NHCOR$_2$ or —NR$_3$R$_4$ where R$_2$ is hydrogen or loweralkyl, and R$_3$ and R$_4$ are independently hydrogen, loweralkyl or cycloalkyl; R is hydrogen, loweralkyl or loweralkylcarbonyl; and R$_1$ is hydrogen, loweralkyl, aryl, diloweralkylaminoloweralkyl, arylloweralkyl, furylloweralkyl, thienylloweralkyl, pyridinylloweralkyl, diarylloweralkyl, oxygen-bridged arylloweralkyl or oxygen-bridged diarylloweralkyl; a stereo, optical or geometrical isomer thereof, or a pharmaceutically acceptable acid addition salt thereof and a suitable carrier therefor.

2. The pharmaceutical composition as defined in claim 1, which comprises an effective amount of N-hydroxy-1,2,3,4-tetrahydro-9-acridinamine.

3. The pharmaceutical composition as defined in claim 1, which comprises an effective amount of N-methoxy-1,2,3,4-tetrahydro-9-acridinamine.

4. The pharmaceutical composition as defined in claim 1, which comprises an effective amount of N-benzyloxy-1,2,3,4-tetrahydro-9-acridinamine.

5. The pharmaceutical composition as defined in claim 1, which comprises an effective amount of N-[(2-phenylethyl)oxy]-1,2,3,4-tetrahydro-9-acridinamine.

6. The pharmaceutical composition as defined in claim 1, which comprises an effective amount of N-hydroxy-7,8,9,10-tetrahydro-6H-cyclohepta[b]quinolin-11-amine.

7. The pharmaceutical composition as defined in claim 1, which comprises an effective amount of 2,3-dihydro-N-hydroxy-1H-cyclopenta[b]quinoline-9-amine.

8. A method of enhancing the cholinergic function in a mammal which comprises administering to a mammal in need of cholinergic function enhancement an effective cholinergic function enhancing amount of a compound of the formula

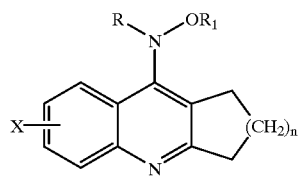

wherein n is 1–4; X is hydrogen, loweralkyl, cycloalkyl, loweralkoxy, halogen, hydroxy, nitro, trifluoromethyl, formyl, loweralkylcarbonyl, arylcarbonyl, —SH, loweralkythio, $NHCOR_2$ or —$NR_3R_4$ where $R_2$ is hydrogen or lowaralkyl, and $R_3$ and $R_4$ are independently hydrogen, loweralkyl or cycloalkyl; R is hydrogen, loweralkyl or loweralkylcarbonyl; and $R_1$ is hydrogen, loweralkyl, aryl, diloweralkylaminoloweralkyl, arylloweralkyl, furylloweralkyl, thienylloweralkyl, pyridinylloweralkyl, diarylloweralkyl, oxygen-bridged arylloweralkyl or oxygen-bridged diarylloweralkyl; a stereo, optical or geometrical isomer thereof, or a pharmaceutically acceptable acid addition salt thereof.

9. The method as defined in claim 8, which comprises the administration of an effective amount of N-hydroxy-1,2,3,4-tetrahydro-9-acridinamine.

10. The method as defined in claim 8, which comprises the administration of an effective amount of N-methoxy-1,2,3,4-tetrahydro-9-acridinamine.

11. The method as defined in claim 8, which comprises the administration of an effective amount of N-benzyloxy-1,2,3,4-tetrahydro-9-acridinamine.

12. The method as defined in claim 9, which comprises the administration of an effective amount of N-[(2-phenylethyl)oxy]-1,2,3,4-tetrahydro-9-acridinamine.

13. The method as defined in claim 10, which comprises the administration of an effective amount of N-hydroxy-7,8,9,10-tetrahydro-6H-cyclohepta[b]quinoline-11-amine.

14. The method as defined in claim 11, which comprises the administration of an effective amount of 2,3-dihydro-N-hydroxy-1H-cyclopenta[b]quinolin-9-amine.

* * * * *

UNITED STATES PATENT AND TRADEMARK OFFICE
CERTIFICATE OF CORRECTION

PATENT NO.    : 6,248,750 B1
DATED         : June 19, 2001
INVENTOR(S)   : Shutske et al.

It is certified that error appears in the above-identified patent and that said Letters Patent is hereby corrected as shown below:

Column 2,
Line 30, reads "group, a phenyl" and should read as -- group, or a phenyl --.
Line 36, reads "Idweralkyl" and should read as -- loweralkyl --.

Column 3,
Line 26, reads "OC(=O)R $_5$" and should read as -- OC(=O)R$_5$ --.
Line 63, reads "acetylchlinesterase" and should read as -- acetylcholinesterase --.

Column 4,
Line 22, reads "srong" and should read as -- strong --.

Column 6,
Line 6 to 7, reads "N-(benzyloxy)-1,2,3,4-tetrahydro-9-acridlnamine" and should read as -- N-(benzyloxy)-1,2,3,4-tetrahydro-9-acridinamine --.
Lines 48-50, reads "N-Methoxy-N-methyl-1,2,3,4-tetrahydro-9-acridinamnine hydrochloride" and should read as -- N-Methoxy-N-methyl-1,2,3,4-tetrahydro-9-acridinamine hydrochloride"
Line 51, reads "9-chloro-1,2,3,4-tetmhydroacridine" and should read as -- 9-chloro-1,2,3,4-tetrahydroacridine --.

Column 7,
Line 14, reads "9-chloro-1,2,3,4-tetrthydroacridine" and should read as -- 9-chloro-1,2,3,4-tetrahydroacridine --.

Column 8,
Line 5, reads "acetate/dichloromethane" and should read as
-- acetate/dichloromethane) --.

Column 9,
Line 14, reads "lowaralkyl" and should read as -- loweralkyl --.

UNITED STATES PATENT AND TRADEMARK OFFICE
CERTIFICATE OF CORRECTION

PATENT NO. : 6,248,750 B1
DATED : June 19, 2001
INVENTOR(S) : Shutske et al.

It is certified that error appears in the above-identified patent and that said Letters Patent is hereby corrected as shown below:

Column 10,
Line 11, reads "in claim 9" and should read as -- in claim 8 --.
Line 14, reads "in claim 10" and should read as -- in claim 8 --.
Line 17, reads "in claim 11" and should read as -- in claim 8 --.

Signed and Sealed this

First Day of October, 2002

Attest:

JAMES E. ROGAN
Attesting Officer  Director of the United States Patent and Trademark Office